(12) United States Patent
Manalis et al.

(10) Patent No.: US 9,134,294 B2
(45) Date of Patent: *Sep. 15, 2015

(54) METHOD AND APPARATUS FOR HIGH THROUGHPUT DIAGNOSIS OF DISEASED CELLS WITH MICROCHANNEL DEVICES

(75) Inventors: Scott Manalis, Cambridge, MA (US); Thomas Burg, Goettingen (DE); Subra Suresh, Wellesley, MA (US); Ken Babcock, Santa Barbara, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 435 days.

This patent is subject to a terminal disclaimer.

(21) Appl. No.: 12/927,031

(22) Filed: Nov. 3, 2010

(65) Prior Publication Data

US 2011/0124095 A1 May 26, 2011

Related U.S. Application Data

(62) Division of application No. 11/620,230, filed on Jan. 5, 2007, now abandoned.

(60) Provisional application No. 60/757,287, filed on Jan. 9, 2006.

(51) Int. Cl.
| | |
|---|---|
| *C12M 1/34* | (2006.01) |
| *G01N 33/50* | (2006.01) |
| *G01N 15/10* | (2006.01) |
| *G01N 33/543* | (2006.01) |

(52) U.S. Cl.
CPC ........ *G01N 33/5005* (2013.01); *G01N 15/1056* (2013.01); *G01N 33/5091* (2013.01); *G01N 33/54366* (2013.01); *G01N 2015/1043* (2013.01)

(58) Field of Classification Search
CPC .......... G01N 33/5005; G01N 33/5091; G01N 33/54366; G01N 15/1056; G01N 2015/1043; G01N 2015/105; G01N 9/002
USPC ........... 435/287.1, 287.2, 288.5, 288.7, 293.1
See application file for complete search history.

(56) References Cited

U.S. PATENT DOCUMENTS

| | | | | |
|---|---|---|---|---|
| 5,486,335 | A * | 1/1996 | Wilding et al. | 422/400 |
| 8,312,763 | B2 * | 11/2012 | Manalis et al. | 73/61.72 |
| 8,631,685 | B2 * | 1/2014 | Manalis et al. | 73/61.75 |
| 8,635,911 | B2 * | 1/2014 | Son et al. | 73/579 |
| 2004/0038426 | A1 * | 2/2004 | Manalis | 436/514 |

* cited by examiner

*Primary Examiner* — William H Beisner
(74) *Attorney, Agent, or Firm* — Mark Rodgers

(57) ABSTRACT

The method and apparatus of the present invention detects changes in cell biomechanics caused by any of a variety of diseases and conditions. In one embodiment, the method and apparatus of the invention detect infection of red blood cells. In one embodiment, the invention is a method and apparatus comprising a microfluidic channel with a constriction, for trapping infected red blood cells while allowing healthy red blood cells to deform and pass through the channel. In another embodiment, the invention comprises a suspended microchannel resonator for detecting and counting red blood cells at the constriction of the microfluidic channel.

1 Claim, 7 Drawing Sheets

Figure 1:
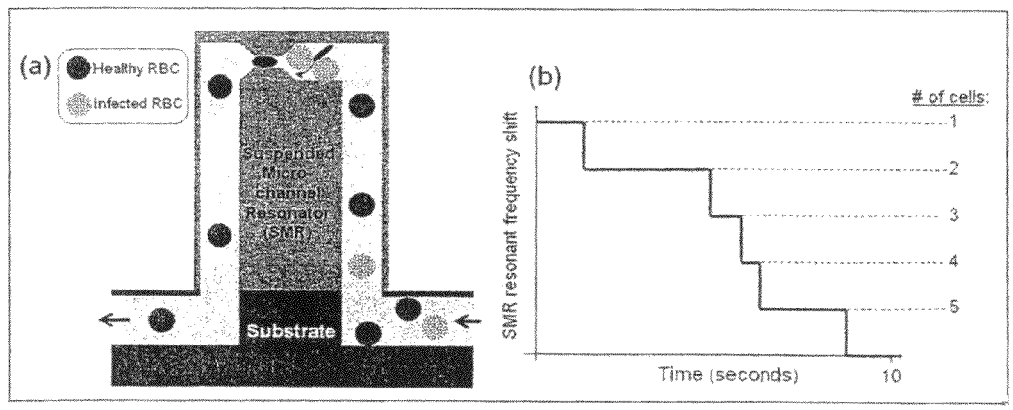

METHOD AND APPARATUS FOR HIGH THROUGHPUT DIAGNOSIS OF DISEASED CELLS WITH MICROCHANNEL DEVICES

RELATED APPLICATIONS

This application is a divisional application of US application U.S. Ser. No. 11/620,230, filed Jan. 5, 2007, now abandoned, which in turn claims priority to U.S. provisional application 60/757,287, filed Jan. 9, 2006

BACKGROUND OF THE INVENTION

This application claims priority to provisional application Ser. No. 60/757,287 filed Jan. 9, 2006, the contents of which are incorporated herein by reference.

Cell-based screening plays an important role in the detection of disease and abnormalities, as well as drug and treatment discovery. Easy and early detection still continues to be essential to treatment of disease infection.

For example, malaria infects about 400 million people each year and kills up to 3 million, most of them African children. The highest mortality is caused by the *Plasmodium falciparum* parasite and its merozoites (daughters) through infection of red blood cells ("RBCs"). See Ref. 5. Better tools are needed for the control and cure of malaria, but malaria remains a diagnostic challenge to laboratories in most countries. Recent efforts at intervention would benefit real time feedback on their efficacy, which has increased the need for rapid diagnostics. At the same time the higher cost of new drug treatments creates downward pressure on diagnostic costs.

To have practical impact, diagnostics that provide confirmation of suspected acute malaria in less than 1 hour would be preferred. See Ref. 6. Several techniques are currently in use, but none are ideal. See id.; see also Ref. 9. Microscopic examination of stained blood samples is currently the standard and yields fast results, but requires a high skill level and is not suitable for mass screening in endemic areas. Polymerase chain reaction ("PCR") and fluorescent labeling methods are sensitive but take a long time for detection, use specialized equipment, and are expensive. A recent generation of "dipstick" or cassette-based immunochromatographic assays, known as Rapid Diagnostic Tests ("RDTs") have helped move diagnosis into the field. See, e.g., Ref. 10. However, these RDTs are influenced by positive results due to causes other than malaria antigenemia, and by negative results due to causes other than low parasitemia. See id. In addition, significant issues have arisen with quality control, reliability, sensitivity to variations in temperature and humidity, shelf life, and overall cost of RDTs. These issues have led to a substantial and costly effort to establish a supporting infrastructure in certain endemic countries. See Ref. 9. Many of these issues are intrinsic to the chemistry-based assay of the RDTs. The goal of mass screening in endemic countries is far from being met.

Thus, there remains a need for cost-effective diagnostic techniques that can yield unambiguous and (semi-) quantitative results in less than an hour with detection sensitivities of less than 100 parasites/$\mu$L (i.e., the goals set forth by the World Health Organization). See Refs. 6 and 9. Even greater sensitivity and quantitative measures of parasitemia are important when monitoring treatment of chronic cases, confirming cure (parasitemia of zero), and monitoring resistance to drugs, a growing and costly problem in malaria treatment.

While challenges associated with rapid detection and the need for innovative solutions are particularly acute in the case of malaria, there is likewise a need in the art for improved methods and apparatus for the diagnosis and/or monitoring of a wide variety for diseases and abnormal conditions.

SUMMARY

The method and apparatus of the present invention detects changes in cell biomechanics due to disease infection. In various embodiments, the present invention is a method and apparatus for providing a sample containing cells obtained from a subject, flowing the cells through at least a portion of a microchannel, and detecting abnormal trapping of one or more of the cells in the microchannel. In one embodiment, the microchannel comprises a constriction to facilitate and/or detect abnormal trapping. In another embodiment, the microchannel comprises receptors to facilitate and/or detect abnormal trapping.

BRIEF DESCRIPTION OF CERTAIN PREFERRED EMBODIMENTS OF THE INVENTION

Figure 2:
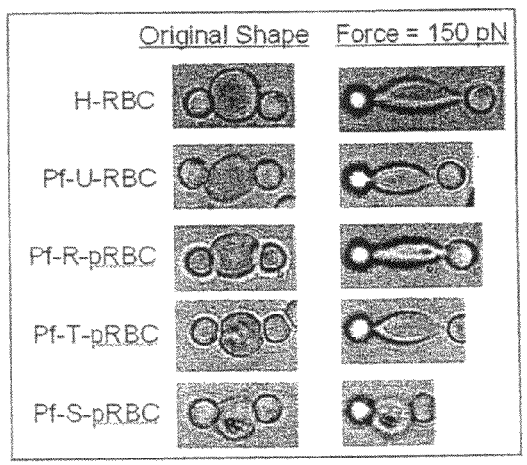
Figure 3:
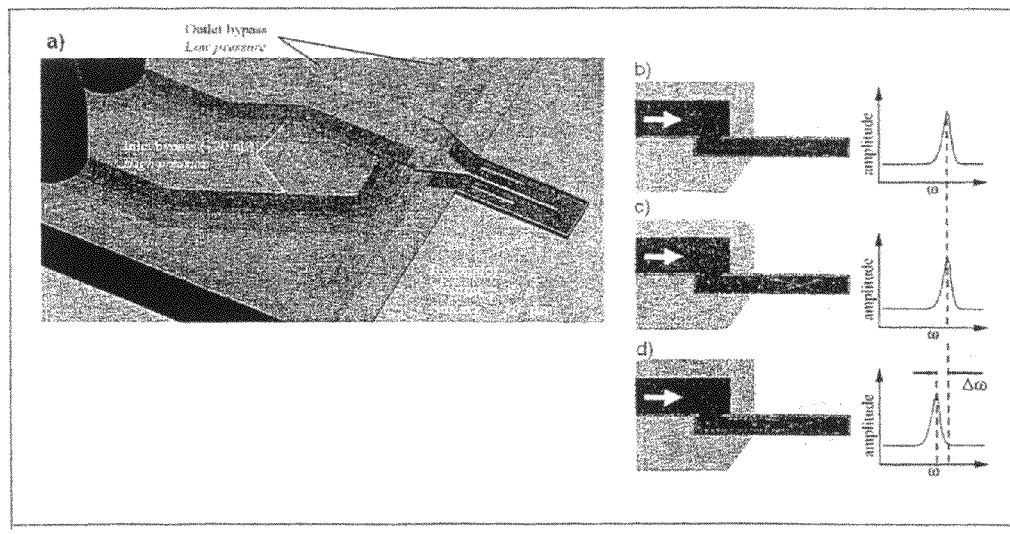
Figure 4:
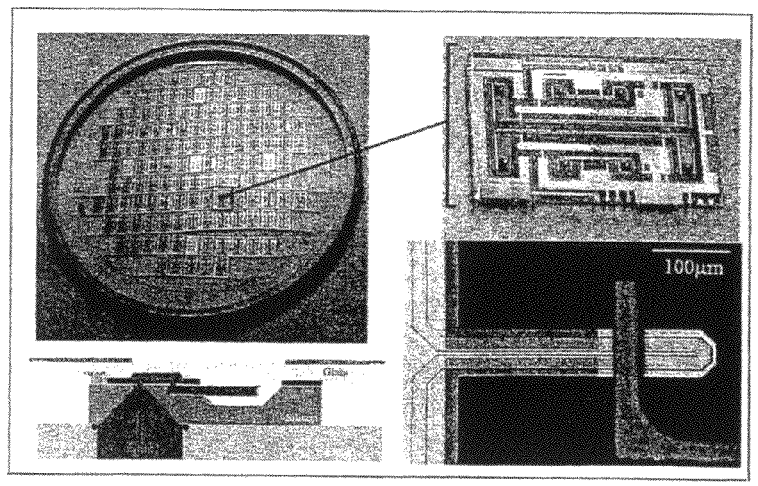
Figure 5:
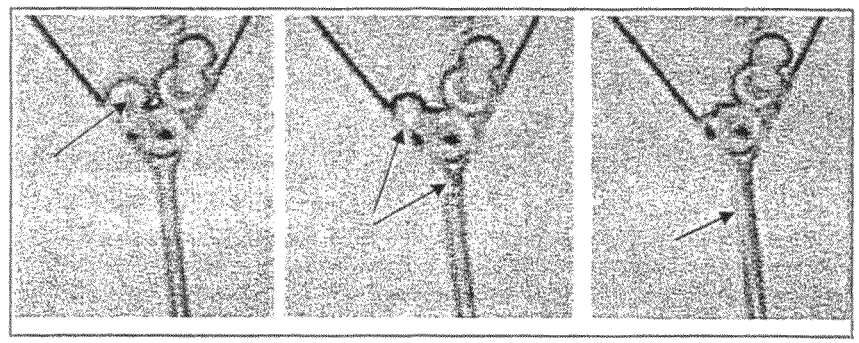
Figure 6:
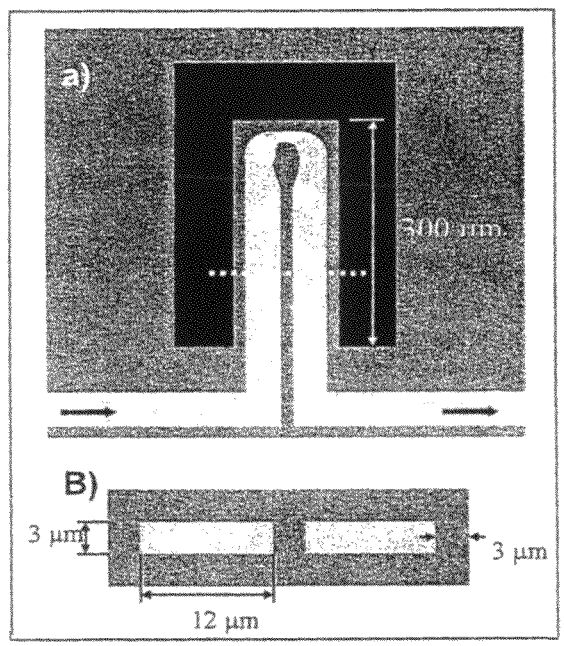
Figure 7:
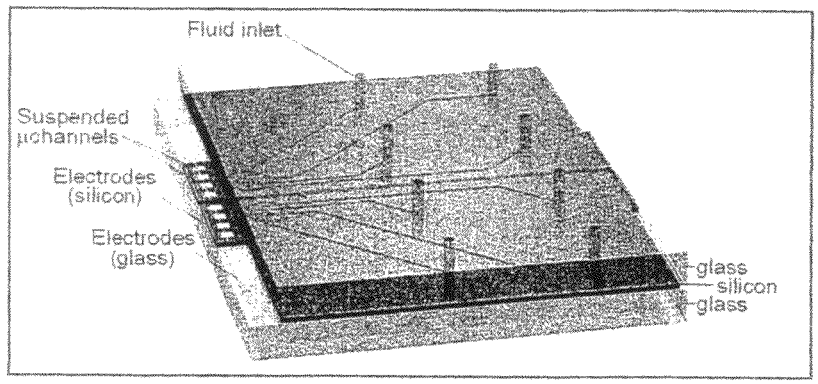
Figure 8:
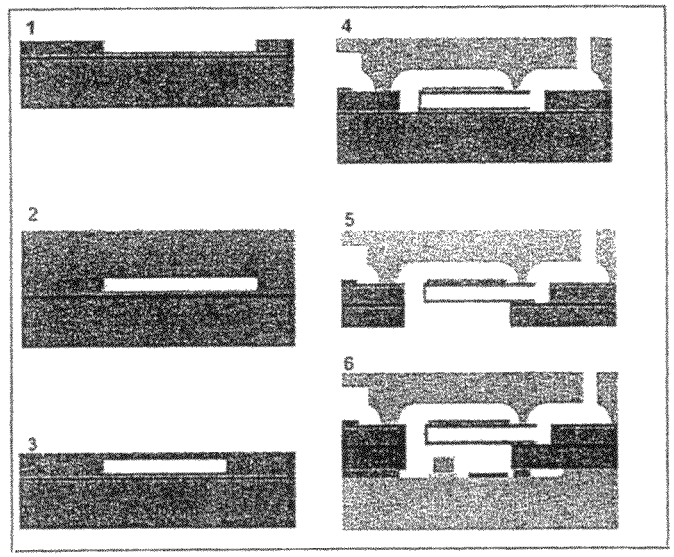
Figure 9:
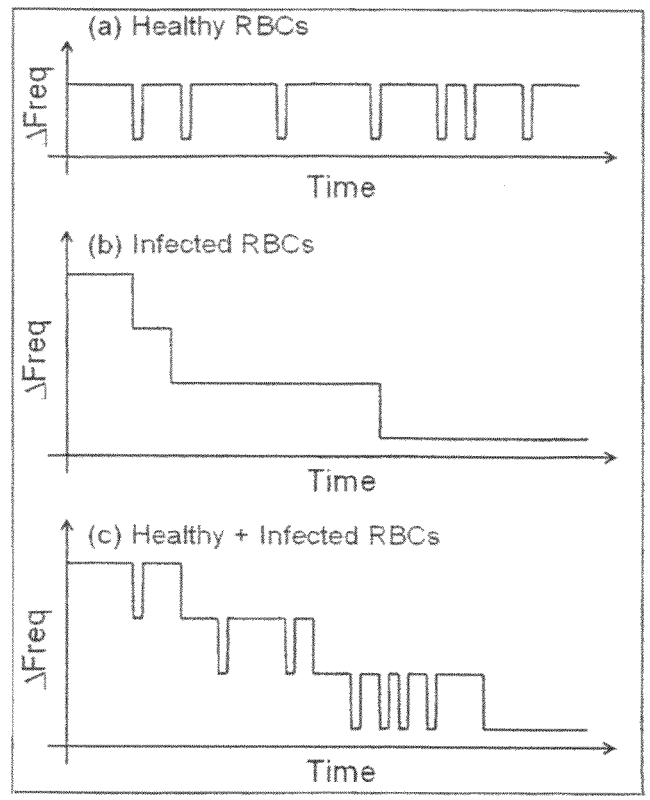
Figure 10:
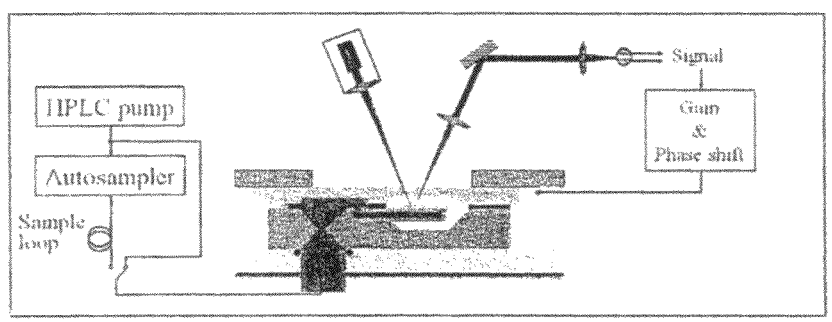
Figure 11A:
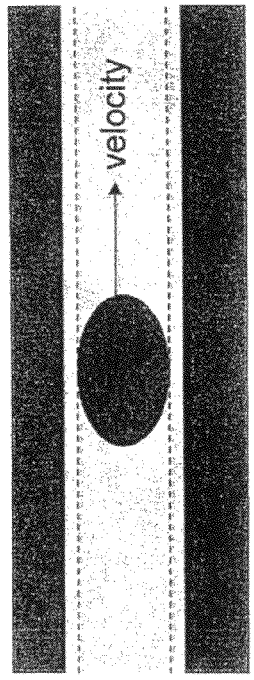
Figure 11B:
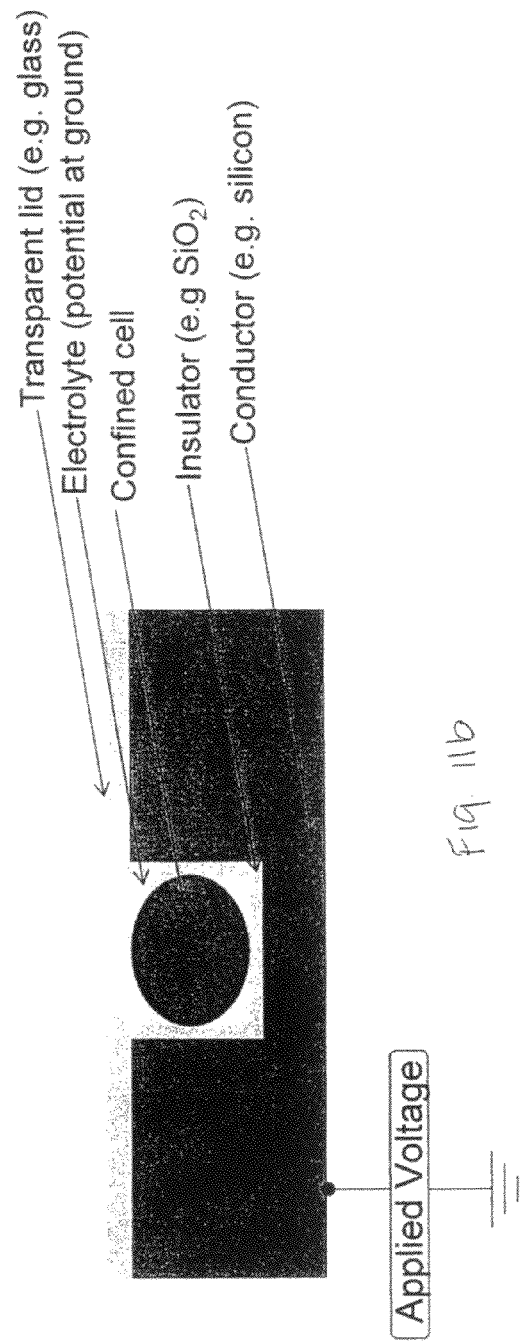
Figure 12:
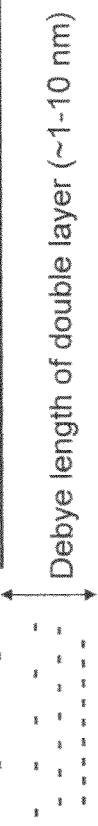
Figure 12:
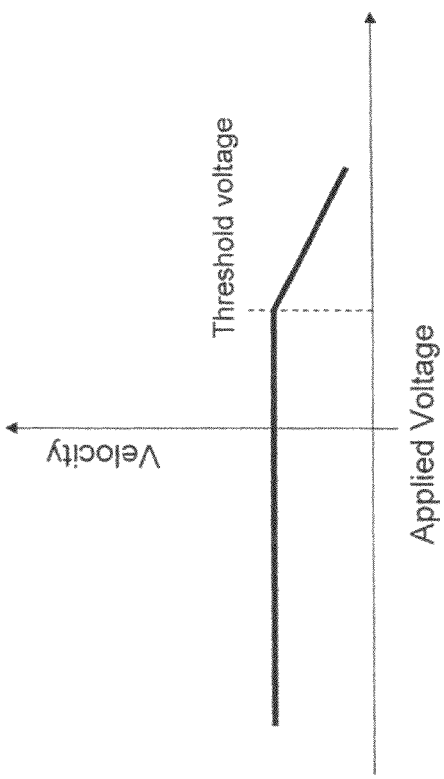

FIG. 1*a*. is a schematic of one embodiment of the invention, wherein the SMR is modified to trap infected cells;

FIG. 1*b*. graphs the expected SMR signal as infected cells are trapped at the constriction;

FIG. 2. illustrates the deformation of RBCs under stretching loads;

FIG. 3*a*. depicts target molecules flowing through a vibrating SMR and captured by receptor molecules attached to the interior channel walls;

FIG. 3*b*. shows the cross-section of a vibrating SMR with microchannels of uniform cross-section;

FIG. 3*c*. shows a SMR when a target analyte enters but does not alter the resonant frequency;

FIG. 3*d*. illustrates a SMR as multiple targets bind to immobilized receptors and the high surface concentration lowers the resonant frequency of the SMR;

FIG. 4. illustrates an example of a "1st generation" SMR device;

FIG. 5. depicts a mix of healthy and *P. falciparum*-infected red blood cells flowing through a microchannel constriction;

FIG. 6*a*. illustrates an embodiment of the present invention having the specifications disclosed in Table 2;

FIG. 6*b*. shows a schematic cross-section through the SMR of FIG. 6*a*;

FIG. 7. depicts another embodiment of the present invention constructed from three layers (glass, silicon, glass);

FIG. 8. illustrates by example the first few process steps in fabricating a SMR of one embodiment of the present invention;

FIG. 9*a*. is a schematic graph of the resonant frequency signal expected for healthy red blood cells when flowed through a SMR according to various embodiments of the present invention;

FIG. 9*b*. is a schematic graph of the resonant frequency signal expected for infected red blood cells when flowed through a SMR according to various embodiments of the present invention;

FIG. 9*c*. is a schematic graph of the resonant frequency signal expected for both healthy and infected red blood cells when flowed through a SMR according to various embodiments of the present invention;

FIG. 10. illustrates one embodiment of the present invention comprising an SMR reader setup;

FIGS. 11a and 11b. depict one embodiment of the present invention wherein the cell velocity as it flows through a microchannel indicates an abnormality or infection; and FIGS. 12a and 12b. further illustrates various embodiments wherein controlling the surface charge of the microchannel alters the velocity of the flowing cells.

DETAILED DESCRIPTION OF CERTAIN PREFERRED EMBODIMENTS OF THE INVENTION

As described briefly above, the method and apparatus of the present invention detects changes in cell biomechanics due to any of a variety of diseases or abnormal conditions including, but not limited to, infection by the causative agent of malaria. In various embodiments, the present invention is a method and apparatus for detecting or monitoring a disease or clinical condition in a subject comprising providing a sample containing cells obtained from the subject, flowing the cells through at least a portion of a microchannel, and detecting abnormal trapping of one or more of the cells in the microchannel. It is preferred that the microchannel be part of a suspended microchannel resonator system. For example, the microchannel may comprise a constriction that traps abnormal or diseased cells, and the method and apparatus detects the presence of a diseased or abnormal cell when that cell is trapped by the constriction, and the microchannel detects increase in mass. In various other embodiments, the microchannel may comprise a surface charge that traps (or otherwise affects the velocity of) abnormal or diseased cells flowing through the microchannel, and the microchannel detects the change in surface charge, mass, and/or velocity.

The Biomechanics of an Infected Cell

The mechanical properties of single cells reveals a connection between human (and other animal) disease states and structural changes in cells that are induced by biochemical effects in vivo, or are caused by the invasion of foreign organisms. See Ref. 1. While normal RBCs are highly deformable liquid-filled compartments (see Ref. 4), the elastic modulus, or stiffness, of an RBC can change through progressive stages during the course of a disease or other abnormal condition. For example, the elastic modulus, or stiffness, of an RBC changes many-fold through progressive stages after invasion by a *P. falciparum* merozoite. Recent quantitative experiments using optical tweezers have shown that a 10-fold increase in stiffness occurs at advanced stages after invasion, with measurable increases at earlier to middle stages as well. FIG. 2 shows the deformation of RBCs under stretching loads. The left column includes optical images of RBCs prior to tensile stretching by optical tweezers. The right column includes optical images of RBCs subject to tensile stretching at a constant force of 151+/−20 pN. From top to bottom, the figure shows the following RBC stages: healthy, exposed/uninfected, ring, trophozoite, and schizont for the 3D7 strain of the *P. falciparum* merozoite. The corresponding shear moduli are shown in Table 1.

TABLE 1

RBC Moduli

| RBC Stage | Time After Invasion | Shear Modulus ($\mu N/m$) |
| --- | --- | --- |
| Healthy | N/A | 5.3 |
| Exposed/Uninfected | N/A | 8 |
| Ring | less than 16 hours | 16 |
| Trophozoite | 16-24 hours | 21.3 |
| Schizont | 24-48 hours | 53.3 |

These changes are associated with the structural changes in the merozoite as it undergoes asexual development and multiplication within the RBC, from an early "ring" stage (beginning approximately 30 minutes after invasion) to an intermediate "trophozoite" stage (16-24 hours) as the parasite develops within, to an advanced "schizont" stage (24-40 hours) marked by nuclear division and multiplication for the number of merozoites. Finally, up to 20 merozoites are released, each of which may infect other RBCs. See Ref. 5.

In the trophozite and schizont stages, an infected RBC shows a marked increase in endothelial adhesion as well as the modulus increases discussed above. The adhesion increases are believed to be caused by proteins, introduced to the RBC membrane and cytoskeleton by the parasite, that appears as "knobs" or protrusions on the cell surface in the schizont state. Together, these effects cause mid and late-stage infected RBCs to "sequester" in the microvasculature of major organs. See Ref. 3. Sequestering is thought to lead to many of the symptoms of acute malaria such as respiratory distress, cerebral malaria, hypoglycaemia, and metabolic acidosis. See id.

Notably, RBCs that are exposed to disease such as malaria parasites, but are not actually invaded, also show changes in deformability. As shown in Table 1, exposed but uninfected RBCs can be approximately 50% stiffer than unexposed healthy RBCs. The increase may be due to proteins transported from infected RBCs to an uninfected RBC (e.g., in sequestering region with many infected cells), or from a parasite that comes into contact with the RBC but does not invade it. While optical tweezers and other instrumentation can provide very precise measurements of the biomechanics of individual cells, their throughput is too low to be considered for diagnostics or drug screening. In one embodiment, the present invention is a method and apparatus for the detection of changes in cell biomechanics due to disease or other abnormal conditions, including, but not limited to, infection by parasite or other infectious agents. In another embodiment, the present invention is a method and apparatus for the detection of red blood cell stiffness and/or deformability due to malaria infection. In other embodiments, the present invention detects other diseases including, but not limited to, cancer, infections by viruses, bacteria, protozoa or other parasites, immunological conditions, etc. affecting the stiffness, thickness, and/or "stickiness" of a cell.

In various embodiments, "stickiness" refers to the adhesion properties of a cell. The adhesion properties of a cell depend on abnormality or disease state of that cell. For example, RBCs infected with a malaria parasite become more sticky. While there are techniques for measuring cell adhesion (e.g., pipette aspirators), it is desirable for a method and apparatus of measuring cell adhesion suitable for high throughput measurement of suspended cells.

Detecting Mass with Microchannel Devices

In one embodiment of the present invention, the method and apparatus for detecting changes in cell biomechanics due to disease or other abnormal conditions comprises a suspended microchannel resonator ("SMR"). The SMR is a resonant mass sensor for specific biomolecular detection in a subnanoliter fluid volume. As with other resonant mass sensors (e.g., the quartz crystal microbalance ("QCM")), the SMR of the present invention can detect the amount of captured target molecules via a change in resonance frequency of the microchannel during adsorption. Target molecules may be flowed through a vibrating SMR and captured by receptor molecules attached to the interior channel walls, as shown by example in FIG. 3a. The change in resonance frequency of the vibrating microchannel detects the amount (i.e., mass) of captured target molecules, or molecule mass.

In various embodiments of the present invention, the receptors, targets, and their aqueous environment are confined inside the SMR, while the SMR itself can oscillate at high "quality factor" ("Q") in an external vacuum environment. This set-up yields extraordinarily high mass resolution. For example, FIG. 3b shows the cross-section of a vibrating SMR with microchannels of uniform cross-section. FIG. 3c shows the SMR when a target analyte enters but does not alter the resonant frequency since volume concentration is low. FIG. 3d shows the SMR as multiple targets bind to immobilized receptors (not shown) and the high surface concentration lowers the resonant frequency of the SMR.

The present invention may be used to measure a resolution of ~10,000 proteins within the 30 picoliter sensor volume, or an absolute mass sensitivity of about 16 femtograms in a 1 Hz detection bandwidth (this value takes into account the relative mass of the sample with respect to the fluid environment inside the detector). The results are about 4000 times better than the best QCM measurements, which may result in approximately 63 pg total mass sensitivity at approximately 1 Hz bandwidth, and about 150 times better than the best results using cantilevers immersed in fluid, which may result in approximately 2.5 pg at 1 Hz. The SMR results show significantly higher sensitivity in mass measurement in an aqueous environment.

Screening for Abnormalities or Disease with Microchannel Devices

In various embodiments, the method and apparatus of the present invention comprises an SMR modified to incorporate a constriction in the microchannel, with the aim of trapping infected or abnormal cells and detecting their presence and number via the SMR frequency shift. An abnormality, or condition indicating disease, includes a change in size, stiffness, "stickiness" or other biomechanical property of a cell. Conditions that could result in abnormal or diseased cells could include infection by any of a variety of infectious agents such as viruses, bacteria, protozoa, and/or fungi; and/or absorption of proteins (e.g., immunoglobulins or other proteins present in the blood) to the cell surface. The present invention may be applicable to detecting a wide variety of diseases or abnormal conditions including cancer. In one embodiment, the present invention detects cancers of the hematopoietic system such as leukemia and lymphoma. In another embodiment, the present invention detects a variety of autoimmune diseases. In still other embodiments, the present invention detects a change in cell biomechanics including softening. For example, the present invention may include a constriction or some other mechanism to monitor the flow of cells located before (or in front of) the SMR. The constriction is smaller than the dimensions of healthy cells, thereby trapping the healthy cells before the microchannel. In such an embodiment, only the abnormal or infected cells flow to the SMR, wherein the SMR detects such cells.

In still other embodiments, the method and apparatus of the present invention may be used to monitor the efficacy of therapy or detect reoccurrence of abnormalities or infection. The results of the testing via the present invention can be used to make therapeutic decisions (e.g., decision to initiate therapy, modify therapy, cease therapy, change a dose, change a drug or mix of drugs in a "drug cocktail", or change treatment, etc.). In one embodiment, empiric therapy is administered pending results of additional diagnostic tests. Furthermore, the present invention may be applicable to screening for and/or detecting a probability of disease or abnormality, exposure to chemicals, or any other external factor in which an alteration is caused in the expression of genes that encode cytoskeletal and/or cell surface proteins. Diseases such as cancer, autoimmune diseases, infections, metabolic disorders, nutritional disorders, exposure to toxins, etc. could affect protein profile in blood, which in turn could cause changes in cell properties such as stiffness, size, adherence, "stickiness", or other biomechanical properties that are detectable using the apparatus and method of the present invention. In still other embodiments, the method and apparatus could detect alterations in hematopoietic cells and/or detect circulating cells that may originate from a tumor and enter the blood stream in small numbers. In yet other embodiments, the method and apparatus of the present invention may be used for the detection of disease or abnormality, or to detect and monitor cells (e.g., cell lines) cultured in vitro.

In another embodiment, the cell is within a sample, wherein the sample is blood, urine, CSF, synovial fluid, and/or any other bodily fluid containing cells, fine needle aspirate, or tissue samples processed to release individual cells. A filter or equivalent may be optionally used to remove lymphocytes or other blood cells that are larger than erythrocytes within a sample.

In another embodiment, the invention can be used to detect individual abnormal or diseased cells or to detect disease or abnormalities on a cell population basis. For example, the method and apparatus of the invention may comprise flowing a sample of blood through an SMR, wherein diseased or abnormal cells are trapped within the SMR and the disease or abnormality is detected based upon the change in resonant frequency of the SMR.

A constriction according to the present invention is a point within the channel wherein there exists a reduction in cross-sectional area. The cross-section of the channel may take any shape and dimensions. For example, the channel may have a cylindrical cross-sectional area, having a diameter in the range of 0-20 μm. The constriction may comprise a range of both cross-sectional area and length. The term "channel" refers to a hole of constant or systematically varied cross-sectional area through a material. Generally a channel has a defined cross-sectional geometry, which may be rectangular, ovoid, circular, or one of those geometries with an imposed finer feature, such as indentations, etc. In various embodiments wherein the channel has a rectangular, square, polygonal, hexagonal, etc. cross-sectional area, the channel comprises a height, width and length dimension as shown by example in FIG. 3b. For example, in one embodiment, the microchannel the height and width (or diameter) of the cell, and the constriction is approximately 10-100% of the width or diameter of the cell. For example, in one embodiment wherein the cell is a RBC, the channel may be a rectangle, having the dimensions of approximately 3 μm by 12 μm, and wherein the dimensions at a constriction is approximately 3 μm by 2-5 μm. In other embodiments, the channel may comprise more than one constriction, wherein optionally each constriction has a distinct cross-sectional area. In still other embodiments, the dimensions of a constriction is selected to trap cells having a particular size, stiffness, or other biomechanical property of interest.

Furthermore, the SMRs of the present invention may further comprise "receptors" (e.g., antibodies or other specific binding agents) attached to the walls of the channels that would bind to ligands that are selectively expressed on the surface of target cells (e.g., abnormal and/or diseased cells) to either permanently or transiently trap the cells. The receptors may add to or replace the constriction function of the microfluidic channels. For example, the receptors may replace the constriction within the SMR, to enable the detection of diseases that cause alteration in expression of cell surface protein(s) while not necessarily altering biomechanical properties such as stiffness. In one aspect of these embodiments, receptors comprise polyclonal or monoclonal antibodies (wherein "antibody" should be understood in a broad sense to refer to antibody fragments, single chain antibodies, or any protein comprising one or more antigen-binding domains), aptamers, peptides selected using phage display technology, lectins, affibodies, etc. In other aspects, rolling of T-lymphocytes on endothelial surfaces involves interactions of glycoprotein ligands for P-selectin and integrin on the cell with receptors on endothelial surfaces. A variety of diseases could lead to alterations of such interactions. In the example of *P. falciparum* malaria, the expression of specific *Plasmodium falciparum* erythrocyte membrane proteins and knob assisted histidine rich protein, and the interactions of these proteins with specific receptors on endothelial surfaces affects adhesion, deformability, and sequestration.

In still other embodiments, the present invention is a method and apparatus for detecting or monitoring a disease or clinical condition in a subject comprising providing a sample containing cells obtained from a subject, flowing the cells through at least a portion of a microchannel; and detecting abnormal trapping of one or more of the cells in the microchannel. "Abnormal trapping" may be defined as trapping that differs from that which would occur if a sample obtained from a subject not suffering from the disease or clinical condition was subjected to the method. Flowing the cells through at least one portion of the microchannel may comprise introducing the cell to the microchannel. If the cell experiences biomechanical changes due to abnormalities or infection, the cell will be introduced into the microchannel, but only flow through a portion of the microchannel, until the abnormal or diseased cell becomes "stuck" within the microchannel (either at the constriction or location of other prohibitory means).

In one embodiment, abnormal trapping is evidenced by a change in velocity. As shown in FIGS. 11*a* and 11*b*, if a cell travels through a microchannel of dimensions equivalent to (or smaller than) that of the cell size, the cell velocity depends on the surface state of the cell membrane and the surface state of the microchannel. The present invention may control the surface charge of the microchannel (as shown in FIGS. 12*a* and 12*b*), or alternatively may control the molecular functionality of the microchannel, in order to determine the velocity of a cell and correlate the velocity to an abnormality or infection. In these embodiments, the cell membrane surface is dependent on disease state. In other embodiments, receptors attached to the microchannel alters the velocity of the flowing cells.

The invention further contemplates using channels other than microchannels, such as "macrochannels" comprising a porous mesh, network of materials, or particles/beads, etc. that would impede the traverse of cells. In certain examples of these embodiments, the abnormal cell is not a sickle cell, nor suffer from sickle cell anemia or sickle cell trait. In one embodiment, the subject suffers from or is suspected of suffering from infection by a malaria parasite. In another embodiment, the subject suffers from cancer. In various other embodiments, the sample comprises red blood cells.

Screening for *P. falciparum* with the SMR

As discussed above, the stiffness of disease-infected cells can be up to an order of magnitude higher than that of healthy RBCs. Previous experiments have demonstrated that healthy RBCs can easily deform and pass through a channel constriction, while infected and stiffened cells are trapped. See Ref. 8. In various embodiments, the method and apparatus of the present invention comprises an SMR modified to incorporate a constriction in the microchannel, with the aim of trapping infected RBC's and detecting their presence and number via the SMR frequency shift that results from retaining trapped RBCs in the microchannel. One embodiment of the concept is shown schematically in FIG. 1*a*, wherein the SMR is modified to trap infected RBCs. FIG. 1*b* graphs the expected SMR signal as infected RBCs are trapped at the constriction and results in a clear and discrete downward step in SMR resonant frequency. In certain embodiments of the present invention, the SMR enables a literal count of infected RBCs and diagnosis of disease (e.g., malaria) with only a few infected cells or even a single event.

In certain embodiments, the present invention does not require functionalization with biochemical reagents found in other biomolecular detection methods and devices. The method and apparatus of the present invention utilizes a "geometrical" approach to trapping and detecting infected RBCs. This approach obviates the need for any reagent chemistries, a potentially significant simplification that will increase robustness, shelf life, and reliability in field use, as compared to certain Rapid Diagnostic Tests (RDTs) whose use has been proposed for detecting malaria. In addition, in certain embodiments, the detection scheme of the present invention is not cross-sensitive to the antigenemia of other diseases.

Instead, various embodiments of the SMR method and apparatus of the present invention may potentially be cross-sensitive to diseases that manifest stiffening or significant morphology changes in RBCs, such as sickle cell anemia and elliptocytosis. The prevalence of such diseases may correlate geographically with malaria. For example, heredity elliptocytosis is seen in 0.6% of the population of equatorial Africa, and the sickle trait is seen in up to 25% of the population in west and central Africa, with ~1% of babies born with some form of the disease. Nonetheless, since these diseases are easily diagnosed by other means, even if such cross-sensitivity exists, it is not expected to have a significant impact on the potential of the method and apparatus of the present invention for detecting malaria. Alternatively or additionally, various embodiments of the SMR may be used to detect any of these conditions and/or to distinguish them from malaria.

In another embodiment of the present invention, the minute differences in cell mass are measured due to the great mass resolution of SMR. For example, in one aspect of this embodiment, the masses of several healthy cells, and the masses of those cells invaded by *P. falciparum* are measured. Statistically significant differences in the mass distributions may, for example, reflect the added mass of the parasites in the infected cells. Furthermore, in another aspect of this embodiment, the method and apparatus detect mass differences between healthy RBCs and those exposed to, but not infected by, *P. falciparum*, the latter of which are thought to absorb proteins from infected cells in their environment, or from external contact with a parasite.

Notably, RBCs in middle and late stages of invasion by *P. falciparum* largely "sequester", i.e., become attached to endothelial linings or clog capillaries, and are rarely found in peripheral blood. See Ref. 5. Significant numbers of RBCs in late stages of infection reappear in peripheral blood only in very late stages of malaria, at which point the disease is nearly always terminal and treatment is ineffectual. In various embodiments, the method and apparatus of the present invention detects cells in earlier (ring) stages of infection, or those in later stages but at extremely low number fraction. In yet another embodiment, the method and apparatus of the present invention combines a microfluidic channel with an antigen-specific assay that specifically binds cells to walls and slows their transit.

In still other embodiments, modifications of the cell trapping concept may allow different species or strains of an infectious agent (e.g., different *Plasmodium* species) to be distinguished from one another. For example, the malaria species *P. vivax* shows an increase in RBC deformability upon infection (see Ref. 3) and could be identified by an RBC's ability to pass through microchannels even smaller than those passable by healthy RBCs. In certain embodiments of the invention, infection by *P. ovale* or *P. malariae* is detected.

Various other factors of a SMR may be modified to improve upon or change the functionality of the present invention. For example, in one embodiment, the SMR further comprises a viscous fluid to control the flow of cells through the microchannel. In another embodiment, the SMR further comprises charge at the surfaces of the microchannel to control the flow of cells.

Fabrication of Suspended Microchannel Resonators

One of the main challenges in implementing and utilizing SMR detection is the fabrication of robust and inexpensive sensors containing micron-scale channels embedded in mechanical resonators. FIG. 4 illustrates an example of a "1st generation" SMR device fabricated in 6 inch wafer format at the Massachusetts Institute of Technology ("MIT") and Innovative Micro Technology ("IMT") containing ~135 SMRs and optical micrograph (right) and cross-section (bottom left) of SMRs that have been vacuum encapsulated. In various embodiments, fabrication is based on lithographic and thin-film deposition and etching techniques capable of forming structures with sub-micron precision. The SMR resonator and interior channels are etched in a silicon wafer, and fluidic and electronic interfaces are accomplished via a Pyrex "capping" wafer. FIG. 4 further shows a single SMR sensor containing a U-shaped microchannel having a 1 micron channel height and an electrode used to drive the resonator into oscillation using electrostatic forces is above the microchannel. Each wafer is diced to produce approximately 135 complete sensor "chips". The scalable batch fabrication of the present invention allows for highly repeatable and cost-effective production, and the Si-based materials yield biocompatible and extremely robust devices.

In certain embodiments, the present invention includes a "2nd generation" SMR device, wherein all fluid interfaces are made from biocompatible materials (e.g., Pyrex and $Si/SiO_2$). These materials yield sensors which are extremely robust mechanically, and which are able to withstand harsh cleaning agents (e.g., Piranha, a mix of sulfuric acid and hydrogen peroxide). In another embodiment, each sensor "chip" has dual sensors for differential detection, which has been shown to be effective at removing signal drift due to thermal variations. In yet another embodiment, the resonators are encompassed in vacuum (~10 mT), giving higher mechanical "Q's" for improved mass sensitivity.

In various embodiments and as depicted in FIG. 10, the method and apparatus of the present invention further comprise a SMR reader for detecting and recording the oscillations of the resonating microchannel. As shown, the reader may comprise a solid state laser and photodetector in an "optical lever" configuration which may be optimized to detect the oscillations. Custom electronics may be combined with commercial frequency counters to detect the resonant frequency. The invention may further comprise a "self-resonant" circuit to maintain the resonator at its fundamental resonant frequency as the total mass varies. Furthermore, the method and apparatus may comprise a PC for system control and a data acquisition card for collecting data. In various embodiments, the SMR may be easily fitted into and removed from the SMR reader. The reader may further comprise simple fluidics interfaces including pumps and valves, through which various solutions (e.g., small RBC samples, wash fluids, etc.) may be injected and kept under constant flow pressure.

It should be noted that where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference.

The following examples contain important additional information, exemplification and guidance that can be adapted to the practice of this invention in its various embodiments and the equivalents thereof.

EXEMPLIFICATION

The method of this invention can be understood further by the examples that illustrate some of the ways by which the inventive apparatus may be constructed, and the method may be practiced. It will be appreciated, however, that these examples do not limit the invention. Variations of the invention, now known or further developed, are considered to fall within the scope of the present invention as described herein and as hereinafter claimed.

Example 1

Microchannel Experiment

As shown in FIG. 5, a mix of healthy and *P. falciparum*-infected RBCs are being flowed through a microchannel constriction. The infected cells are trapped while healthy RBCs easily pass through the congestion of trapped cells.

Example 2

Estimated Mass Resolution and Throughput of a SMR

A single RBC contains 270 million hemoglobins each with a molecular weight 64 kD, giving ~$10^{10}$ kD for the weight of a RBC. The effective mass resolution of the modified SMR will be 200 fG or ~$10^8$ kD. The estimated effective mass resolution takes into account the relative mass density difference between proteins and their surrounding solution. Thus, the SMR signal-to-noise for a single RBC is expected to be ~$10^2$. The anticipated step-wise signal from the SMR using a sample of infected RBCs are shown in FIG. 1b.

Depending on the specific strain of malaria, up to 1-10% of the RBCs in blood volume become infected. See Ref. 5. In 1 uL of blood, there are on the order of one million RBCs. If the blood is diluted by a thousand (1000) fold, the SMR of the present invention is estimated to interrogate approximately 30 cells per second (assuming an ultimate flow rate of 30 nL/sec). If 1% of the cells are infected, approximately 3 cells can be counted in a time period of ten seconds. Even in samples with extremely small fractions of infected cells (approximately 100 per uL), infected cells should be detectable within approximately a few minutes.

Example 3

A SMR for Detecting Cells

An embodiment of the present invention is schematically drawn in FIG. 6a. Specifications for these SMRs are listed in Table 2 below. FIG. 6b depicts a schematic cross-section of the SMR in FIG. 6a.

TABLE 2

| Example "2nd Generation" SMR Specifications | |
|---|---|
| Length | 300 mm |
| Resonant Frequency | 220 kHz |
| Detector Volume | 22 pL |
| Vacuum | <15 mTorr |
| Estimated Quality Factor | >2000 |
| Estimated Frequency Resolution | 0.1 ppm |
| Mass Resolution | 35 fg |
| Mass Resolution for Proteins | ~140 fg |

Sensors are constructed from three layers (glass, silicon, glass), as shown in FIG. 7. The intermediate silicon layer (dark grey) contains the resonating cantilever with an embedded microfluidic channel. The top glass layer contains fluidic ports and allows optical access. The bottom glass layer contains drive electrodes and seals the vacuum chambers containing the resonators. Total chip size is approximately 8×12 mm. The general MEM fabrication process is explained in detail in U.S. patent application Ser. No. 10/699,883 to Manalis, et al., incorporated herein by reference. Furthermore, FIG. 8 illustrates by example the first few process steps of one embodiment of the present invention, used to define the channel shape.

In this example, the process begins with a "Silicon-on-Insulator" ("SOI") configuration in which a silicon oxide layer (grey) is sandwiched between two silicon wafers. The top silicon layer is etched to a well-defined depth using reactive-ion etching, a standard MEMs processing technique in which plasma etches away silicon. A channel of desired lateral shape is created by using a mask through which the plasma ions pass during etching. The channel depth is controlled via the duration of etching. The "2nd generation" mask defines a U-shaped channel of nearly uniform cross-section of approximately 8 micron width.

A portion of the channel shape is modified using a modified mask for the silicon etch step. Although most of the embedded channel is 8 microns wide and 3 microns high, a constriction is created near the end of the channel in which the width of the channel is narrowed to 3 microns.

Example 4

Testing Single RBC Sensitivity

Prior to testing with RBCs, the SMR is treated by flowing 1% w/v bovine serum albumin ("BSA") in phosphate buffered saline ("PBS") for approximately 5 minutes. The pretreatment minimizes sticking of RBCs to the microchannel walls. Healthy RBCs at a concentration of 5000 cells/µL of PBS are flowed through the SMR at a flow rate of approximately 0.1 nL/sec at constant pressure. The approximately 22 pL volume of the SMR is exchanged once every approximately 200 ms, and on average on RBC flows through the resonator every 2 seconds. Simultaneously, the SMR frequency signal is monitored at a bandwidth of 10 Hz. Notably, the flow rate used for demonstrating sensitivity is much lower than is necessary for detecting infected cells, since the SMR response must be measured during a healthy cell's brief transit time through the SMR. As shown in FIG. 9a, a momentary decrease in resonant frequency is seen due to the mass of each RBC as it flows through the resonator. The effective signal to noise ratio for a single RBC is measured by comparing the resonant frequency of the healthy cell with the noise floor of the SMR. Signal to noise ratio should be greater than 3.

Example 5

Demonstrating the Detection of Infected RBCs

Asexual blood stages of *P. falciparum* are synchronized using a plasmagel treatment, followed by an alanine treatment, and then cultured by incubation at 37° C. in RPMI 1640 medium supplemented with human serum under an atmosphere of 5% carbon dioxide and low oxygen (1%). Two samples are tested. The first sample is cultured for a duration of 12-16 hours, the time required for infection to develop to the ring stages of *P. falciparum* with approximately 3 times increase in stiffness as compared with healthy RBCs. The second sample is cultured for a duration of approximately 36 hours, the time required for the RBCs to develop into a schizont state with approximately 10 times increase in stiffness.

The RBCs are diluted to 100 cells/µL in PBS and flowed through the SMR at an approximate flow rate of 10 nL/sec. On average, one cell flows through the SMR each second. The SMR frequency signal is monitored at a bandwidth of 10 Hz. As shown in FIG. 9b, the resonant frequency continues to decrease as the cells are trapped and the total mass increases. The total frequency decrease is a measure of the number of infected cells that are trapped. Clear steps in the response and a low noise floor confirms that RBCs are trapped and that the sensor resolution is ample to detect single infected cells. These measurements have superior signal-to-noise compared to those of healthy RBCs which pass through momentarily because the infected cells remain in the SMR and can be detected continuously once trapped. The flow rate can be monitored under constant pressure. Substantial flow will persist despite some flow reduction due to the pile up of infected RBCs behind the microchannel constriction.

Example 6

Detection of Infected RBCs in a Background of Healthy RBCs

A combination of healthy RBCs and infected RBCs cultured as described above are mixed to a desired proportion, diluted with PBS, and flowed through the SMR. Infected cells are trapped while healthy cells can deform and squeeze by the infected cells to exit the SMR. As shown in FIG. 9c, the events that return to the local baseline indicate healthy cells passing through the resonator, while those with a persistent frequency offset indicate trapped, infected cells.

Example 7

SMR Reusability

After trapping several infected RBCs, the SMR is flushed by reversing the flow, with the sample removed via an alternative exit channel. A return of the SMR resonant frequency to its original value will indicate that the trapped cells have been flushed. The SMR is then flushed with PBS for approximately 2 minutes and the RBC experiment is repeated to verify reusability.

In an alternative example, the channel is cleared by flushing with an aggressive etchant, e.g., piranha (sulfuric acid and hydrogen peroxide). The return of the SMR resonant frequency to zero will indicate that trapped cells are dissolved and flushed. The SMR is then flushed with PBS and the RBC experiment is repeated to verify reusability.

Example 8

High Throughout

A mix of healthy and infected RBCs are flowed through the SMR at a rate of at least 3 cells/second and detection within 1 minute is verified for 1% infected fraction.

REFERENCES

1. D. Boal, *The mechanics of the cell*. Cambridge, UK: Cambridge University Press, 2002.
2. T. P. Burg and S. R. Manalis, *Suspended microchannel resonators for biomolecular detection*, Applied Physics Letters, 83 (2003) p. 2698.
3. A. M. Dondorp, P. A. Kager, J. Vreeken, N. J. White, Parasitol. Today 16 (2000) p. 228.
4. E. Evans, Methods Enzymol. 173 (1989) p. 3.
5. L. H. Miller, D. I. Baruch, K. March, and O. K. Daumbo, *The pathogenic basis for malaria*, Nature, 415 (2002) p. 228.
6. A. Moody, *Rapid Diagnostic Tests for Malaria Parasites*, Clinical Microbiology Reviews, 15 (2002) p. 66.
7. Q-Sense; www.q-sense.com; the quoted value assumes a 7 mm$^2$ detector surface, as listed for the D300 QCM.
8. J. P. Shelby, J. White, K. Ganesan, P. K. Rathod, and D. T. Chiu, *A microfluidic model for single cell capillary obstruction by Plasmodium falciparum-infected erythrocytes*, PNAS 100 (2003) p. 14618.
9. World Health Organization Meeting Report, *Malaria rapid diagnosis: making it work*, WHO Regional Office for the Western Pacific and http://www.who.int/malaria/cmc_upload/0/000/016/750/rdt2.pdf (2003).
10. World Health Organization web site, *Malaria rapid diagnostic tests*, http://www.wpro.who.int/rdt/; and, *The uses of malaria diagnostic tests*, http://www.wpro.who.int/rdt/docs/RDTGuidelines_final.pdf Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. As used herein, the term "approximately" means that the measurement or number may deviate by 10% from the numeral given. Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more limitations found in any other claim that is dependent on the same base claim. Furthermore, where the claims recite an apparatus, it is to be understood that methods of using the apparatus as described in any of the claims reciting methods are also disclosed, unless it would be evident to one of ordinary skill in the art that a contradiction or inconsistency would arise. It is also to be understood that where the claims recite an apparatus that has particular features or characteristics, the invention encompasses an apparatus comprising means for implementing such features or characteristics. In addition, it is to be understood that any particular embodiment of the present invention that falls within the prior art may be explicitly excluded from the claims. Since such embodiments are deemed to be known to one of ordinary skill in the art, they may be excluded even if the exclusion is not set forth explicitly herein.

What is claimed is:

1. An apparatus for detecting or monitoring a disease or clinical condition in a subject comprising:
a suspended microchannel resonator, comprising an oscillating substrate, with at least one fixed end and a region of high sensitivity away from the fixed end, and at least one microchannel, which is fabricated with channel dimensions sized to allow unrestricted flow of target cells, wherein a sample containing target cells obtained from the subject are flowed through at least a portion of the microchannel, and;
at least one constriction fabricated in the microchannel, in the region of high sensitivity, wherein the constriction dimensions are sized and positioned to impede the flow of target cells in the region of high sensitivity of the microchannel.

* * * * *